United States Patent [19]

Oka

[11] Patent Number: 5,752,913

[45] Date of Patent: May 19, 1998

[54] PHYSICAL INFORMATION MONITOR SYSTEM HAVING MEANS FOR DETERMINING REFERENCE RANGE FOR ABNORMALITY DETERMINATION OF THE MONITORED INFORMATION

[75] Inventor: Tohru Oka, Ichinomiya, Japan

[73] Assignee: Colin Corporation, Komaki, Japan

[21] Appl. No.: 714,810

[22] Filed: Sep. 17, 1996

[51] Int. Cl.[6] ........................................ A61B 5/00
[52] U.S. Cl. ............................. 600/300; 600/485
[58] Field of Search ........................ 128/630, 668, 128/672, 900, 920, 923; 600/300, 481, 485

[56] References Cited

U.S. PATENT DOCUMENTS

| 4,712,562 | 12/1987 | Ohayon et al. | 128/672 |
|---|---|---|---|
| 5,279,303 | 1/1994 | Kawamura et al. | 128/683 |
| 5,564,427 | 10/1996 | Aso et al. | 128/681 |

FOREIGN PATENT DOCUMENTS

| A-237-588 | 9/1987 | European Pat. Off. . |
| A-649-629 | 4/1995 | European Pat. Off. . |
| A-329-306 | 8/1989 | France . |
| A-2-679-675 | 1/1993 | France . |
| A-2-694-421 | 2/1994 | France . |
| A-2-700-684 | 7/1994 | France . |
| WO-94/13198 | 6/1994 | WIPO . |

*Primary Examiner*—William E. Kamm
*Assistant Examiner*—George R. Evanisko
*Attorney, Agent, or Firm*—Oliff & Berridge, PLC

[57] ABSTRACT

The physical information monitoring system includes a physical information obtaining device for successfully obtaining present physical information of a living subject, an identification code input device for determining an identification code which identifies the living subject, a physical information memory device for storing previous physical information which was previously obtained from the living subject prior to operation of physical information obtaining device, and a reference range determining device for determining a reference range used to determine whether the presently obtained physical information for the living subject identified by the identification code is abnormal. The reference range determining device determines the reference range on the basis of the previous physical information stored in the memory device. The system further includes an abnormality indicating device for generating an abnormality signal which indicates that the present physical information is abnormal, if the present physical information is outside of the reference range.

5 Claims, 4 Drawing Sheets

PHYSICAL INFORMATION MONITOR SYSTEM HAVING MEANS FOR DETERMINING REFERENCE RANGE FOR ABNORMALITY DETERMINATION OF THE MONITORED INFORMATION

BACKGROUND OF THE INVENTION

1. Field of the Invention

The present invention relates to a physical information monitor system for monitoring successively obtained physical information of living subjects.

2. Discussion of the Related Art

For monitoring the physical condition of a patient (living subject) in an operating room or ICU (Intensive Care Unit), there is proposed a physical information monitor system adapted to successively measure one or more physical parameters of the patient, such as blood pressure, pulse rate, blood oxygen saturation and temperature, and to generate an abnormality signal indicative of abnormality of any physical parameter when the physical parameter is outside a predetermined reference range.

It is generally desired to properly determine the reference range used for correctly monitoring the physical information of the patient, so as to quickly inform a medical worker of any abnormality of the patient with high reliability. However, since the physical information varies to a considerable extent depending upon individual patients, it is not appropriate to apply the same reference range for monitoring the physical information of different patients. In other words, it is difficult to determine the reference range that can be suitably used for the different patients. In view of this, the reference range is conventionally determined for each of the patients by the medical worker, on the basis of the physical information of the patient obtained prior to the monitoring operation. However, this determination of the reference range inevitably requires experience and skill or knowledge of the medical worker. The thus determined reference range is often required to be modified after the commencement of the monitoring operation.

SUMMARY OF THE INVENTION

It is therefore an object of the present invention to provide a physical information monitor system which is capable of automatically determining an appropriate reference range of a physical parameter for monitoring physical information of a living subject.

The above object may be attained according to a principle of the present invention which provides a physical information monitor system comprising: (a) physical information obtaining means for successively obtaining physical information of a living subject; (b) identification code input means for entering an identification code which identifies the living subject; (c) physical information memory means for storing the physical information which is previously obtained from the living subject prior to operation of the physical information obtaining means; (d) reference range determining means for determining a reference range used to determine whether the physical information obtained by the physical information obtaining means for the living subject identified by the identification code is abnormal or not, the reference range determining means determining the reference range on the basis of the physical information stored in the physical information memory means; and (e) abnormality indicating means for generating an abnormality signal which indicates that the physical information obtained by the physical information obtaining means is abnormal, if the physical information obtained by the physical information obtaining means is outside the reference range.

According to this arrangement, when the identification code which identifies a specific living subject is read by the identification code input means, the physical information of the subject which is previously obtained prior to the monitoring operation of the present system is read out from the physical information memory means. Subsequently, the reference range determining means determines the reference range for determining whether the physical information obtained during the present monitoring operation is abnormal or not. This determination is effected on the basis of the physical information which has been obtained prior to the monitoring operation and which has been read out from the physical information memory means. The abnormality indicating means is adapted to generate the abnormality signal indicative of abnormality of the physical information obtained during the monitoring operation if the physical information obtained by the physical information obtaining means is outside the determined reference range.

In the physical information monitor system according to the present invention, the reference range used for monitoring the physical information is automatically and suitably determined by the reference range determining means, on the basis of the previously obtained physical information which is read out from the physical information memory means. Accordingly, the system does not require experience and skill or knowledge of the medical worker in determining the reference range used for monitoring the physical information of the patient. Further, the reference range determined according to the present invention is not required to be modified in the process of the monitoring operation.

According to a preferred form of the present invention, the identification code input means comprises a card reader which reads the identification code stored in a card-like recording medium. In this arrangement, the identification code can be inputted more easily and more accurately than in a case wherein the identification code is entered through a keyboard.

According to one advantageous arrangement of the above preferred form of the present invention, the physical information memory means is constituted by a portion of a memory area of the card-like recording medium, and the card reader receives the recording medium to read the physical information previously obtained prior to the operation of the physical information obtaining means. This arrangement wherein the physical information of the living subject is stored in the card-like recording medium provided for each living subject does not require a memory device for storing the physical information of the individual living subjects.

According to another advantageous arrangement of the above preferred form of the present invention, the physical information memory means comprises a data memory device which stores the physical information of a plurality of living subjects obtained prior to the operation of the physical information obtaining means, and the reference range determining means receives from the data memory device the physical information of one of the plurality of living subjects which is identified by the identification code which is stored in the card-like recording medium and which is read by the card reader. In this arrangement, a well-known magnetic card with a simple structure having a strip-like magnetic memory area can be used as the recording medium for storing the identification code. Namely, the present arrangement does not require an expensive IC card for storing the physical information of the living subjects as well as their identification codes.

BRIEF DESCRIPTION OF THE DRAWINGS

The above and optional objects, features and advantages of the present invention will be better understood by reading the following detailed description of a presently preferred embodiment of the invention when considered in connection with the accompanying drawings in which.

DETAILED DESCRIPTION OF THE PREFERRED EMBODIMENT

Figure 1:
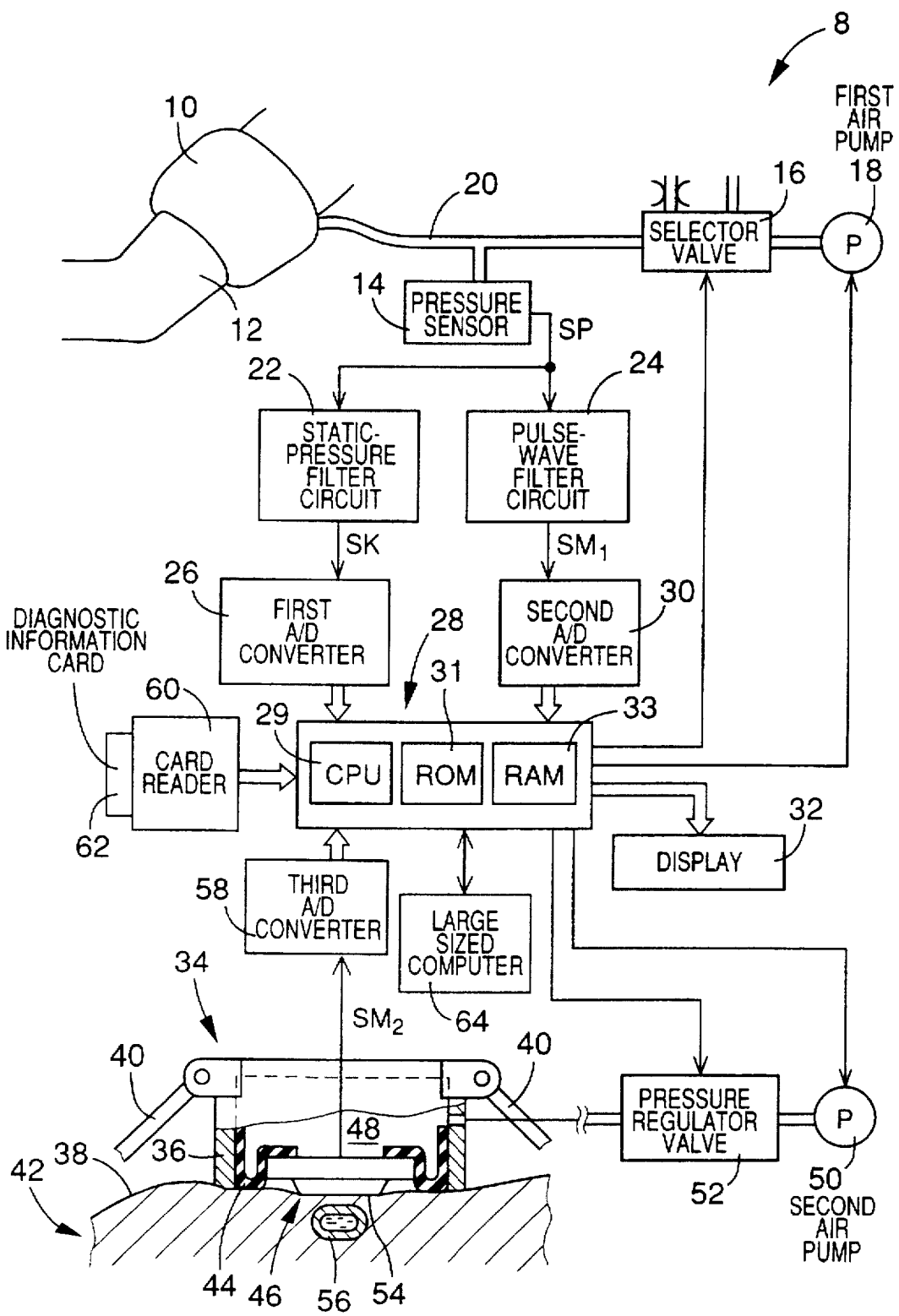
FIG. 1 is a diagrammatic block diagram of a blood pressure monitor system according to one embodiment of the present invention.

Referring first to FIG. 1, there is shown a blood pressure (BP) monitor system 8 constructed according to one embodiment of the present invention. In FIG. 1, the reference numeral 10 denotes an inflatable cuff constituted by an elongate fabric bag and a rubber bag accommodated in the elongate fabric bag. The cuff 10 is worn on a patient such that it is wound on an upper arm 12 of the patient, for example. A pressure sensor 14, a selector valve 16 and a first air pump 18 are connected to the cuff 10 via a conduit piping 20. The selector valve 16 is selectively placed in an inflation position, a slow-deflation position, and a rapid-deflation position. In the inflation position, the selector valve 16 permits pressurized air to be supplied from the first air pump 18 to the cuff 10. In the slow-deflation position, the selector valve 16 permits the pressurized air to be slowly discharged from the cuff 10. In the rapid-deflation position, the selector valve 16 permits the pressurized air to be rapidly discharged from the cuff 10.

The pressure sensor 14 detects an air pressure in the cuff 10 and supplies an electric signal SP representative of the detected pressure to a static-pressure filter circuit 22 and a pulse-wave filter circuit 24. The static-pressure filter circuit 22 has a low-pass filter and transmits a static component of the signal SP as a cuff-pressure signal SK to a control device 28 via a first analog to digital (A/D) converter 26.

The pulse-wave filter circuit 24 has a band-pass filter and transmits an oscillating component of the signal SP as a cuff pulse wave signal $SM_1$ to the control device 28 via a second analog to digital (A/D) converter 30. The cuff pulse wave signal $SM_1$ is representative of a pulse wave, i.e., an oscillatory pressure wave which is produced from a brachial artery of the patient in synchronism with the heartbeat of the patient and transmitted to the cuff 10. In the present embodiment, the cuff 10, pressure sensor 14 and pulse-wave filter circuit 24 cooperate with each other to function as a pulse wave sensor for obtaining the blood pressure of the patient.

The control device 28 is constituted by a so-called microcomputer which includes a central processing unit (CPU) 29, a read only memory (ROM) 31, a random access memory (RAM) 33 and an input and output (I/O) port not shown. The CPU 29 performs signal processing operations according to control programs stored in the ROM 31 by utilizing a temporary data storage function of the RAM 33, and generates drive signals through the I/O port so as to control the selector valve 16 and first air pump 18.

The present monitor system 8 further includes a pulse wave probe 34. The probe 34 is set on a wrist 42 located downstream of the arterial vessel of either one of the two upper arms 12, on which the cuff 10 is worn or is not worn. The probe 34 includes a container-like housing 36 which is detachably set on a body surface 38 of the wrist 42 with a pair of bands 40, 40 fastened round the wrist 42, such that the open end of the housing 36 contacts the body surface 38 of the wrist 42. A pulse wave sensor 46 is supported by the housing 36 via a flexible diaphragm 44, such that the pulse wave sensor 46 is displaceable relative to the housing 36 and is movable out of the housing 36 through its open end. The housing 36, diaphragm 44 and pulse wave sensor 46 cooperate with each other to define a pressure chamber 48, to which pressurized air is supplied from a second air pump 50 via a pressure regulator valve 52. Thus, the pulse wave sensor 46 is pressed against the body surface 38 with a pressing force $P_{HD}$ corresponding to an air pressure in the pressure chamber 48.

The pulse wave sensor 46 includes a plurality of semiconductor pressure-sensing elements (not shown) provided on one of opposite surfaces of a semiconductor substrate consisting of a single crystal of silicon, which one surface serves as a contact surface 54 of the pulse wave sensor 46. The pulse wave sensor 46 is pressed at the contact surface 54 against the body surface 38 of the wrist 42, to detect the oscillatory pressure wave, i.e., pulse wave, which is produced by a radial artery 56 and transmitted to the body surface 38 and the contact surface 54. The pulse wave sensor 46 generates a probe pulse wave signal SM2 representative of the detected pulse wave. The probe pulse wave signal SM2 is supplied to the control device 28 via a third analog to digital (A/D) converter 58.

The CPU 29 of the control device 28 operates according to the control programs stored in the ROM 31, for applying drive signals to the second air pump 50 and the pressure regulator valve 52 so as to adjust the air pressure in the pressure chamber 48, in other words, to adjust the pressing force PHD of the pulse wave sensor 46 which acts on the body surface 38. In monitoring the blood pressure of the patient, the CPU 29 determines an optimum pressing force $P_{HDP}$ of the pulse wave sensor 46, on the basis of the pulse waves obtained while the air pressure in the pressure chamber is continuously changed. The pressure regulator valve 52 is controlled so as to maintain the air pressure in the pressure chamber 48 at an optimum level corresponding to the determined optimum pressing force $P_{HDP}$.

The present monitor system 8 further has a card reader 60 for reading information on a diagnostic information card 62 inserted therein. The card reader 60 is adapted to send the information to the control device 28. In the diagnostic information card 62, there are stored an identification code which identifies a specific living subject or patient (hereinafter referred to as "patient") and blood pressure data obtained during resting of the living subject when the patient received a medical diagnosis before the patient is subjected to blood pressure monitoring operation by the present BP monitor system 8. The physical information such as previously obtained blood pressure values may be stored for each patient in a large-sized computer 64 installed in a hospital, for example.

Figure 3:
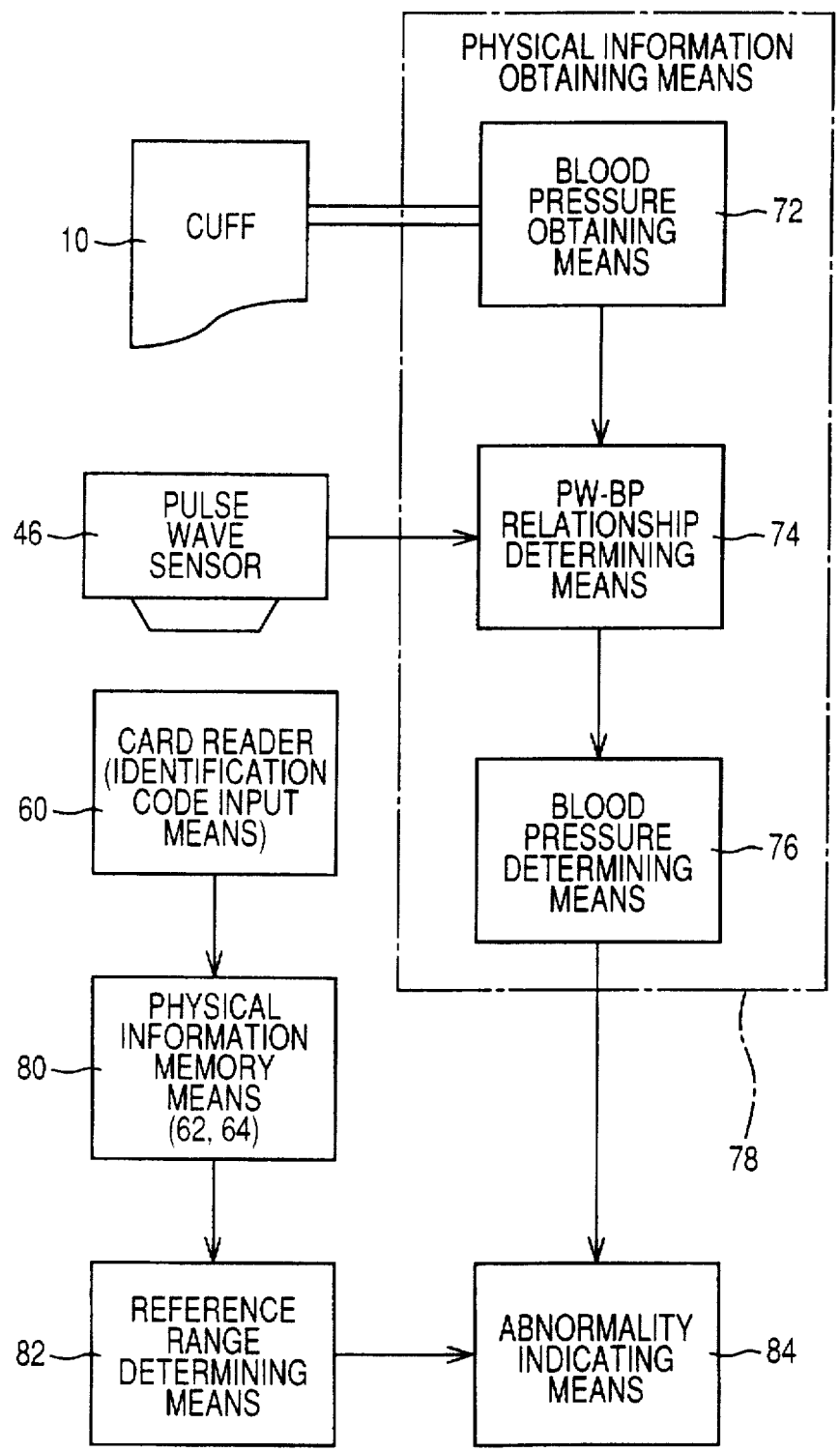
FIG. 3 is a block diagram schematically showing various functions of a control device used in the blood pressure monitor system of FIG. 1.

FIG. 3 illustrates various functions of the control device 28 of the present BP monitor system 8, which includes the above-indicated cuff 10, pulse wave sensor 46 and card reader 60. The BP monitor system 8 further includes physical information obtaining means 78, physical information memory means 80, reference range determining means 82 and abnormality indicating means 84. The physical information obtaining means 78 incorporates blood pressure (BP) obtaining means 72 adapted to obtain a systolic blood pressure (SAP) and a diastolic blood pressure (DAP) of the patient according to a known oscillometric method (JIS T 1115). Described in detail, after the pressure in the cuff 10 is first increased up to a predetermined target value (e.g., about 180 mmHg) higher by a suitable amount than an expected or estimated systolic blood pressure of the patient, the pressure in the cuff 10 is slowly lowered at a rate of about 3 mmHg/sec. The SAP and DAP values are determined on the basis of a change in the magnitudes of successive pulses of the pulse wave obtained by the pulse-wave filter circuit 24 while the pressure in the cuff 10 is slowly lowered. When the blood pressure measurement is completed, the pressure in the cuff 10 is released.

The pulse wave sensor 46 is preferably worn on the wrist 42 of one of the arms 12 of the patient on which the cuff 10 is not wound, so that the pulse wave sensor 46 is pressed against the body surface 38 of the wrist 42 to detect the pulse wave generated from the radial artery of the wrist.

The physical information obtaining means 78 further incorporates relationship determining means 74 adapted to determine a relationship between a magnitude PM of the pulse wave detected by the pulse wave sensor 46 and the blood pressure determined by the BP obtaining means 72. The relationship between the pulse wave magnitude PM and the blood pressure (hereinafter referred to as "PW-BP relationship") is indicated in a graph of FIG. 2 by way of example, and represented by the following equation:

MBP=A.PM+B, wherein

MBP: monitored blood pressure;

A: a constant which represents a gradient; and

B: a constant which represents an intercept.

The physical information obtaining means 78 further incorporates blood pressure determining means 76 adapted to determine a monitored systolic blood pressure MBPSY and a monitored diastolic blood pressure $MBP_{DIA}$ according to the determined PW-BP relationship, based on the magnitude PM of each pulse wave detected by the pulse wave sensor 46, i.e., on the basis of a maximum pulse wave magnitude (upper peak) $P_{M2max}$ and a minimum pulse wave magnitude (lower peak) $P_{M2min}$. The determined blood pressure values MBP ($MBP_{SYS}$ and $MBP_{DIA}$) are indicated on a display 32. Thus, the physical information obtaining means 78 is adapted to obtain the blood pressure as an example of physical information of the living subject.

The card reader 60 which functions as identification code input means reads in the identification code stored in the diagnostic information card 62 which is one example of a recording medium in the form of a card. The physical information memory means 80 is constituted by a portion of the memory area of the card 62 or by the large-sized computer 64 functioning as a data memory device. The memory means 80 stores the physical information of the patient which was obtained prior to the physical information monitoring of the patient by the present BP monitor system 8. The physical information stored in the memory means 80 was obtained during resting of the patient identified by the identification code when the patient received medical diagnosis or treatment prior to the present monitoring operation. Usually, the physical information stored in the memory device 80 is obtained when the patient is in a comparatively normal condition. In the present embodiment, the blood pressure is the physical information representative of the physical condition of the patient.

When the patient's identification code is read out from the diagnostic information card 62 by the card reader 60, the reference range determining means 82 determines a reference range used for judging whether the blood pressure values successively obtained by the BP measuring means 72 during the present BP monitoring period are abnormal or not, based on the data stored in the diagnostic information card 62 or large-sized computer 64 indicative of the blood pressure values obtained during resting of the patient prior to the present monitoring operation. In the present embodiment, the reference range is determined or defined by upper and lower limits which are equal to ±20% of an average of the stored blood pressure values. In case that the blood pressure values are not stored in the diagnostic information card 62, the determining means 82 determines the reference range by reading out, from the large-sized computer 64, the blood pressure values of the patient identified by the identification code read by the card reader 60.

The abnormality indicating means 84 is adapted to produce an abnormality signal which indicates that the blood pressure values are abnormal when the blood pressure values successively obtained during the current monitoring period by the physical information obtaining means 78 are outside the reference range determined as described above. The physical information abnormality signal may take various forms, such as a signal for activating an optical (visual) device, an audio or voice generating device or other devices for indicating the abnormality.

There will be described the operation of the control device 28 referring to the flow chart of FIG. 4.

Figure 4:
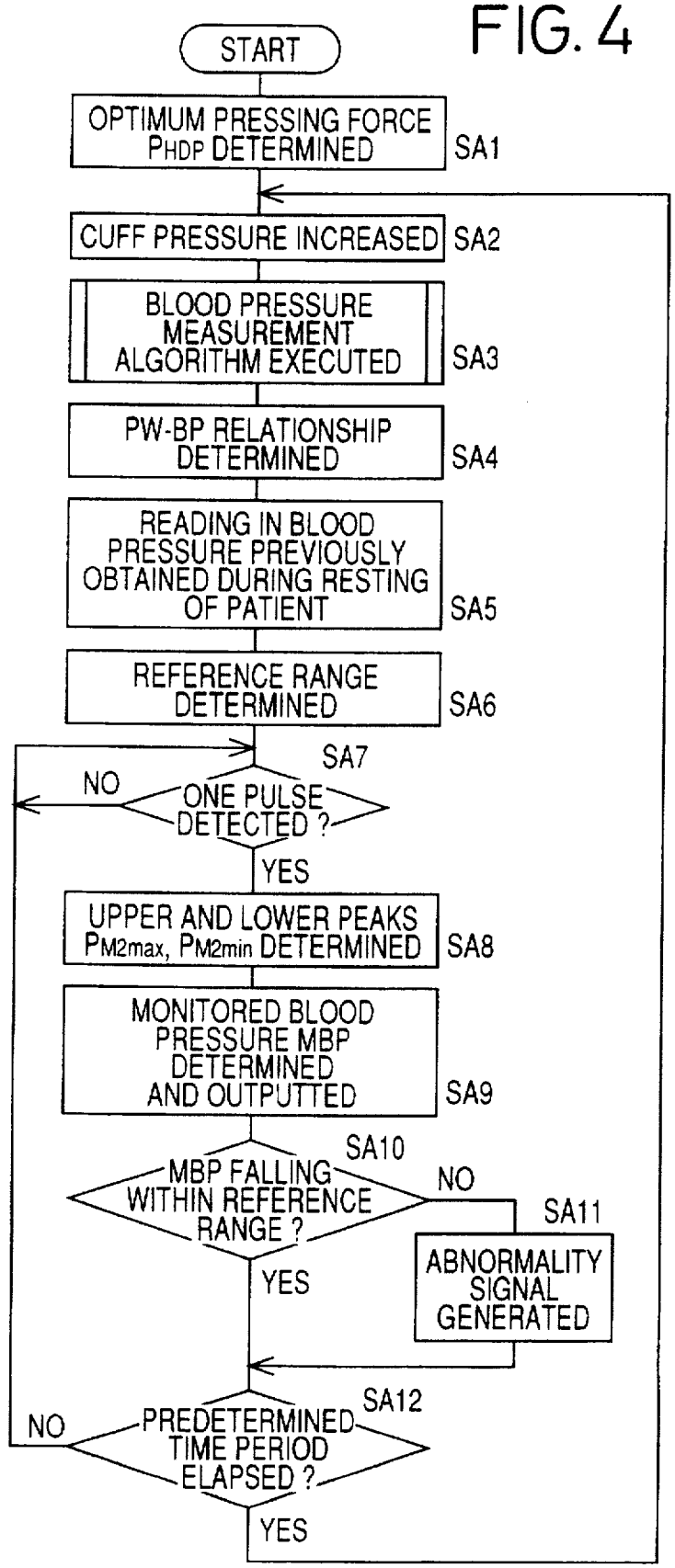
FIG. 4 is a flow chart representing a control routine executed by the control device in the blood pressure monitor system of FIG. 1.

A control routine illustrated in the flow chart of FIG. 4 is initiated with step SA1 in which the air pressure in the pressure chamber 48 is slowly raised, and the CPU 29 determines the optimum air pressure in the pressure chamber 48, at which the amplitude of a pulse detected by the pulse wave sensor 46 is maximized. The air pressure in the chamber 48 is held at the determined optimum level so that the pressing force of the pulse wave sensor 46 is maintained at the optimum value $P_{HDP}$.

Step SA1 is followed by step SA2 in which the pressure in the cuff 10 is raised for effecting the blood pressure measurement in the following step SA3 corresponding to the BP obtaining means 72. In this step SA3, the blood pressure of the patient is measured according to a predetermined blood pressure measuring algorithm. Described in detail, following the increase of the cuff pressure in step SA2, the selector valve 16 is placed in the inflation position and the first air pump 18 is actuated so as to increase the pressure in the cuff 10 up to a target value (e.g., 180 mmHg) higher by a suitable amount than the estimated systolic blood pressure of the patient. Subsequently, the first air pump 18 is turned off and the selector valve 16 is switched from the inflation position to the slow-deflation position so as to slowly decrease the pressure in the cuff 10 at a rate of 3 mmHg/sec. The systolic blood pressure (SAP), mean blood pressure (MAP) and diastolic blood pressure (DAP) are determined based on variation of the amplitudes of successive pulses of the cuff pulse wave signal SM1 obtained during the slow decreasing of the cuff pressure, according to a well-known oscillometric blood pressure determining algorithm, for example. Further, the pulse rate (PR) is determined based on an interval between successive adjacent pulses of the cuff pulse wave signal SM1. The determined SAP, MAP, DAP and PR values are indicated on the display 32, and the selector valve 16 is switched from the slow-deflation position to the rapid-deflation position, whereby the pressure in the cuff 10 is rapidly lowered.

Figure 2:
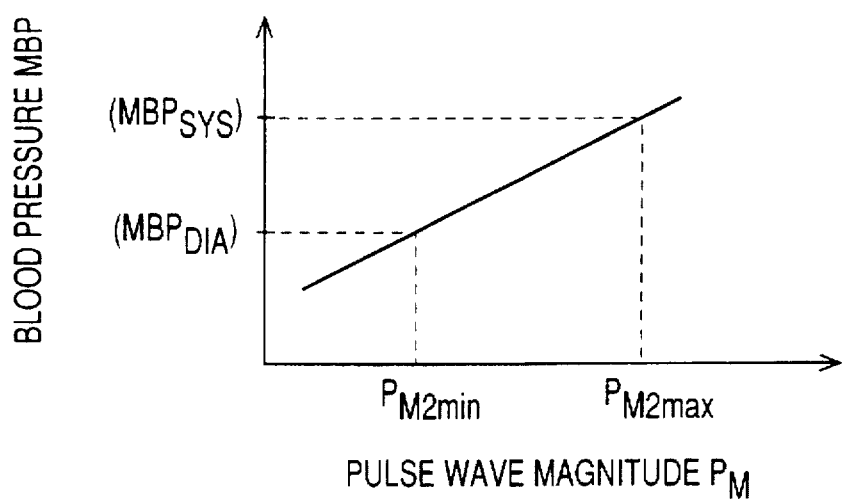
FIG. 2 is a graph representing a relationship between a pulse wave magnitude $P_M$ and a monitored blood pressure MBP.

The control flow then goes to step SA4 corresponding to the PW-BP relationship determining means 74 so as to obtain a relationship between the magnitude (absolute value) of each pulse of the pulse wave detected by the pulse wave sensor 46 (i.e., magnitude of the probe pulse wave signal SM2) and the blood pressure values SAP, DAP measured by using the cuff 10 in step SA3. In other words, one pulse of the probe pulse wave signal SM2 from the pulse wave sensor 46 is read to determine a maximum and a minimum magnitude $P_{M2max}$, $P_{M2min}$ of that pulse. Subsequently, the PW-BP relationship determining means 74 determines the relationship between the pulse wave magnitude PM and the monitored blood pressure MBP as indicated in the graph of FIG. 2, on the basis of the determined maximum and minimum pulse wave magnitudes $P_{M2max}$, $P_{M2min}$, and the systolic and diastolic blood pressure values SAP, DAP obtained by using the cuff 10 in step SA3.

After the PW-BP relationship is obtained as described above in step SA4, step SA5 is implemented to read the identification code stored in the diagnostic information card 62 inserted into the card reader 60, so that the previous blood pressure values of the patient identified by the card 62 are read out from the predetermined memory area of the card 62 or the computer 64 functioning as the physical information memory means 80. The previous blood pressure values stored in the card 62 or the computer 64 were obtained during resting of the patient prior to the present BP monitoring operation.

The control flow then goes to step SA6 corresponding to the reference range determining means 82, in which the reference range for monitoring the blood pressure is determined based on the previously obtained blood pressure values which have been read in step SA5. If the previous systolic blood pressure of the patient obtained during resting is 140 mmHg, the reference range is determined to be a range between ±20% of that previous systolic blood pressure, for instance. In this case, the upper and lower limits of the reference range are automatically determined to be 112 mmHg to 168 mmHg, respectively.

Step SA6 is followed by step SA7 to determine whether one pulse of the probe pulse wave signal SM2 has been supplied from the pulse wave sensor 46. As long as a negative decision is obtained in step SA7, this step is repeatedly implemented. If an affirmative decision is obtained in step SA7, the control flow goes to steps SA8 and SA9 corresponding to the blood pressure determining means 76, so as to determine the maximum and minimum magnitudes (upper and lower peaks) of the pulse of the probe pulse wave signal SM2 received from the pulse wave sensor 46 which is pressed against the body surface 38 with the above-described optimum pressing force $P_{HDP}$. Further, a monitored systolic blood pressure $MBP_{SYS}$ and a monitored diastolic blood pressure $MBP_{DIA}$ are determined based on the maximum and minimum magnitudes $P_{M2max}$ and $P_{M2min}$ of the pulse of the probe pulse wave signal SM2, according to the PW-BP relationship (as shown in the graph of FIG. 2) which has been obtained in step SA4 as described above. The determined monitored systolic and diastolic blood pressure values $MBP_{SYS}$ and $MBP_{DIA}$ are indicated on the display 32, together with the waveform of the pulse.

The control flow then goes to step SA10 to determine whether the determined systolic blood pressure $MBP_{SYS}$ falls within the reference range determined in step SA6. If an affirmative decision is made in step SA10, the control flow goes directly to step SA12. On the other hand, if a negative decision is made in step SA10, step SA11 is implemented to generate an abnormality signal which indicates the systolic blood pressure of the patient is abnormal. Thereafter, the control flow goes to step SA12. The abnormality is visually indicated by a flickering, colored or enlarged area on the display 32. Alternatively, the abnormality signal is used to provide an audible alarm, or to activate any desired devices to indicate the abnormal blood pressure of the patient. In the present embodiment, steps SA10 and SA11 correspond to the abnormality indicating means 84.

Step SA12 following step SA11 is provided to determine whether a time period elapsed after the commencement of the BP measurement by using the cuff 10 in step SA3 is equal to a predetermined value, e.g., several tens of minutes. If a negative decision is obtained in step SA12, the control flow goes back to step SA7. Steps SA7–SA12 are repeatedly implemented, so that the monitored systolic and diastolic blood pressure values $MBP_{SYS}$ and $MBP_{DIA}$ of the individual pulses of the pulse wave signal SM2 are continuously determined and indicated on the display 32. On the other hand, if an affirmative decision is obtained in step SA12, the control flow goes back to step SA2, and the following steps are implemented to update the PW-BP relationship. Thus, the PW-BP relationship used in step SA9 is updated each time the predetermined time has passed, namely, each time the affirmative decision is obtained in step SA10.

According to the present embodiment as described above, when the previously obtained blood pressure values of the patient identified by the identification code stored in the diagnostic information card 62 inserted into the card reader 60 are read out form the physical information memory means 80, the reference range determining means 82 corresponding to step SA6 determines the reference range for determining whether the blood pressure values obtained during the current blood pressure monitoring operation are abnormal or not, on the basis of the previously obtained blood pressure values. The abnormality indicating means 84 corresponding to steps SA10 SA11 produces the abnormality signal indicating the abnormality of the physical information, i.e., the blood pressure, of the patient, when the blood pressure values successively obtained by the physical information obtaining means 78 corresponding to steps SA8 and SA9 are outside the reference range. Thus, in the present embodiment, the reference range used for monitoring the blood pressure is determined based on the blood pressure data obtained during resting of the patient prior to the blood pressure monitoring operation by the present BP monitor system 8. That is, the present arrangement makes it possible to automatically determine a suitable reference range for monitoring the blood pressure of the patient by simply inserting the card 62 into the card reader 60. Accordingly, the reference range can be determined without requiring experience and skill or knowledge of the medical worker. Further, it is not required to modify the reference range in the process of the blood pressure monitoring operation.

In contrast, the conventional blood pressure monitoring operation requires the reference range to be determined by the medical worker on the basis of the blood pressure data obtained prior to the blood pressure monitoring operation. In this case, the determination of the reference range inevitably depends on the experience and skill of the medical worker.

and the thus determined reference range is often required to be modified after the commencement of the blood pressure monitoring operation.

While the present invention has been described in its presently proffered embodiment, it is to be understood that the invention may be otherwise modified.

In the illustrated embodiment, the patient identification code is read out from the card 62 inserted into the card reader 60. However, the identification code may be entered through a keyboard by the medical worker.

In the illustrated embodiment, the reference range is automatically determined so as to monitor the systolic blood pressure (SAP). However, the reference range may be automatically determined so as to monitor the mean blood pressure (MAP) or the diastolic blood pressure (DAP). The reference range may be determined to monitor any physical information other than the blood pressure, such as blood oxygen saturation, temperature or pulse rate of the living subject.

In the illustrated embodiment, the upper and lower limits of the reference range are determined to be ±20% of the average blood pressure value previously obtained during resting of the patient. However, the range may be suitably determined as needed depending upon the specific physical information to be monitored.

In the illustrated embodiment, although the blood pressure data previously obtained during resting of the patient are stored in both of the diagnostic information card 62 and the computer 64, the blood pressure data may be stored in only one of the card 62 and the computer 64.

The blood pressure obtaining means 72 is adapted to determine the blood pressure according to the known oscillometric method, based on a change in the magnitude of the pulses of the pulse wave, which change is detected as the pressure in the cuff 10 is varied. However, the blood pressure obtaining means 72 may be adapted to determine the blood pressure according to the known Korotkoff-sound method in which a microphone is used to detect presence and absence of Korotkoff sounds of an artery as the pressure in the cuff 10 is changed.

It is to be understood that the present invention may be embodied with other changes, improvements and modifications which will occur to those skilled in the art without departing from the scope and spirit of the invention defined in the appended claims.

What is claimed is:

1. A physical information monitor system, comprising:

physical information obtaining means for successfully obtaining present physical information of a living subject;

identification code input means for entering an identification code which identifies said living subject said identification code input means comprising a card reader;

physical information memory means for storing previous physical information which is previously obtained from said living subject prior to operation of said physical information obtaining means, said physical information memory means comprising a card-like recording medium which has a memory area;

reference range determining means for determining a reference range used to determine whether said present physical information obtained by said physical information obtaining means for the living subject identified by said identification code is abnormal or not, said reference range determining means determining said reference range on the basis of said previous physical information stored in said physical information memory means;

abnormality indicating means for generating an abnormality signal which indicates that said present physical information obtained by said physical information obtaining means is abnormal, if said present physical information obtained by said physical information obtaining means is outside said reference range; and wherein said physical information memory means is constituted by a portion of said memory area of said card-like recording medium, and said card reader reads said identification code stored in said card-like recording medium and said previous physical information previously obtained prior to said operation of said physical information obtaining means.

2. A physical information monitor system according to claim 1, wherein said physical information memory means comprises a data memory device which stores previous physical information of a plurality of living subjects obtained prior to the operation of said physical information obtaining means, and said reference range determining means receives from said data memory device said previous physical information of one of said plurality of living subjects which is identified by said identification code which is stored in said card-like recording medium and which is read by said card reader.

3. A physical information monitor system according to claim 1, wherein said physical information obtaining means comprises:

pulse wave detecting means for detecting a pulse wave produced from an artery vessel of said living subject in synchronism with heartbeat of said subject;

blood pressure obtaining means including an inflatable cuff, for obtaining a blood pressure of said living subject;

relationship determining means for determining a relationship between a magnitude of said pulse wave detected by said pulse wave detecting means and said blood pressure obtained by said blood pressure obtaining means; and blood pressure determining means for determining a monitored systolic blood pressure ($MBP_{SYS}$) and a monitored diastolic blood pressure ($MBP_{DIA}$) based on said magnitude of said pulse wave and said relationship determined by said determining means.

4. A physical information monitor system according to claim 1, wherein said present and previous information comprises blood pressure of said living subject.

5. A physical information monitor system according to claim 1, wherein said previous physical information stored in said physical information memory means comprises an average of a plurality of previously obtained physical information values.

* * * * *